(12) United States Patent
Chmiel et al.

(10) Patent No.: US 8,577,450 B1
(45) Date of Patent: Nov. 5, 2013

(54) GRAPHIC INTERFACE FOR MULTI-SPINE PROBE

(75) Inventors: Yoram Chmiel, Kefar Yona (IL); Jaron Breitman, Timrat (IL); Gal Hayam, Tivon (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 13/555,669

(22) Filed: Jul. 23, 2012

(51) Int. Cl.
  *A61B 5/0428* (2006.01)
(52) U.S. Cl.
  USPC .......................................................... 600/523
(58) Field of Classification Search
  USPC ..................... 607/98–102; 600/509, 523–524
  See application file for complete search history.

(56) References Cited

U.S. PATENT DOCUMENTS

| | | | |
|---|---|---|---|
| 4,522,212 A * | 6/1985 | Gelinas et al. | 600/374 |
| 6,226,542 B1 | 5/2001 | Reisfeld | |
| 6,240,307 B1 * | 5/2001 | Beatty et al. | 600/374 |
| 6,301,496 B1 | 10/2001 | Reisfeld | |
| 6,542,773 B2 * | 4/2003 | Dupree et al. | 600/509 |
| 6,814,733 B2 | 11/2004 | Schwartz et al. | |
| 6,892,091 B1 | 5/2005 | Ben-Haim et al. | |
| 6,961,602 B2 | 11/2005 | Fuimaono et al. | |
| 6,997,924 B2 | 2/2006 | Schwartz et al. | |
| 7,156,816 B2 | 1/2007 | Schwartz et al. | |
| 7,536,218 B2 | 5/2009 | Govari et al. | |
| 2007/0060832 A1 | 3/2007 | Levin | |
| 2007/0083193 A1 | 4/2007 | Werneth et al. | |
| 2009/0275828 A1 | 11/2009 | Shachar et al. | |

* cited by examiner

*Primary Examiner* — Amanda Patton
(74) *Attorney, Agent, or Firm* — Wayne C. Jaeschke, Jr.

(57) ABSTRACT

Methods and systems for mapping cardiac electrical activity employ a cardiac catheter having a plurality of spines mounted at the distal end, each spine having a plurality of electrodes. Electrical signal data are obtained from the heart via the electrodes, and respective intracardiac locations and orientations of the spines are sensed. An electroanatomic map of the heart is derived from the signal data, and presented as a graphic representation of the respective intracardiac locations and orientations of the spines, with distinctive graphical indicia of at least portions of the spines. The method is further carried out by displaying the electroanatomic map, and responsively to the displayed electroanatomic map, adjusting at least one of the locations and orientations of at least one of the spines.

5 Claims, 7 Drawing Sheets

GRAPHIC INTERFACE FOR MULTI-SPINE PROBE

BACKGROUND OF THE INVENTION

1. Field of the Invention

This invention relates to invasive medical devices. More particularly, this invention relates to monitoring of electrical activity within the heart using an invasive probe.

2. Description of the Related Art

Cardiac arrhythmia, such as atrial fibrillation, occurs when regions of cardiac tissue abnormally conduct electric signals to adjacent tissue, thereby disrupting the normal cardiac cycle and causing asynchronous rhythm.

Procedures for treating arrhythmia include surgically disrupting the origin of the signals causing the arrhythmia, as well as disrupting the conducting pathway for such signals. By selectively ablating cardiac tissue by application of energy via a catheter, it is sometimes possible to cease or modify the propagation of unwanted electrical signals from one portion of the heart to another. The ablation process destroys the unwanted electrical pathways by formation of non-conducting lesions.

Mapping of electrical potentials in the heart is now commonly performed, using cardiac catheters comprising electrophysiological sensors for mapping the electrical activity of the heart. Typically, time-varying electrical potentials in the endocardium are sensed and recorded as a function of position inside the heart, and then used to map a local electrogram or local activation time. Activation time differs from point to point in the endocardium due to the time required for conduction of electrical impulses through the heart muscle. The direction of this electrical conduction at any point in the heart is conventionally represented by an activation vector, which is normal to an isoelectric activation front, both of which may be derived from a map of activation time. The rate of propagation of the activation front through any point in the endocardium may be represented as a velocity vector.

Mapping the activation front and conduction fields aids the physician in identifying and diagnosing abnormalities, such as ventricular and atrial tachycardia and ventricular and atrial fibrillation, that result from areas of impaired electrical propagation in the heart tissue.

Localized defects in the heart's conduction of activation signals may be identified by observing phenomena such as multiple activation fronts, abnormal concentrations of activation vectors, or changes in the velocity vector or deviation of the vector from normal values. Examples of such defects include re-entrant areas, which may be associated with signal patterns known as complex fractionated electrograms. Once a defect is located by such mapping, it may be ablated (if it is functioning abnormally) or otherwise treated so as to restore the normal function of the heart insofar as is possible.

Mapping of the electrical activation time in the heart muscle requires that the location of the sensor within the heart be known at the time of each measurement. In the past, such mapping was performed using a single movable electrode sensor inside the heart, which sensor measured activation time relative to a fixed external reference electrode. This technique, however, requires calibration, for example impedance calibrations with adjustments for impedance unrelated to that of the body. Mapping of electrical activation time using a single electrode was, furthermore, a lengthy procedure, which was generally performed under fluoroscopic imaging, thereby exposing the patient to undesirable ionizing radiation. Further, in an arrhythmic heart, activation times at a single location may change between consecutive beats.

Because of the drawbacks of single-electrode mapping, a number of inventors have taught the use of multiple electrodes to measure electrical potentials simultaneously at different locations in the endocardium, thereby allowing activation time to be mapped more rapidly and conveniently, as described.

For example, commonly assigned U.S. Pat. No. 6,961,602, which is herein incorporated by reference, describes a catheter comprises a plurality of spines each capable of obtaining electrical, mechanical and locational data. The catheter comprises a mapping assembly having at least two spines, each having a proximal end attached at the distal end of the catheter body and a free distal end. Each spine comprises at least one location sensor and at least one electrode, preferably a tip electrode and at least one ring electrode. The spines may be arranged in an expanded arrangement wherein each spine extends radially outwardly from the catheter body or in a collapsed arrangement wherein each spine is disposed generally along the longitudinal axis of the catheter body. In use, at least one electrode from each spine is positioned in contact with heart tissue to map the electrical activity of the heart. The location sensors are used to determine the location of each point where the electrical activity is monitored.

SUMMARY OF THE INVENTION

There is provided according to embodiments of the invention a method of mapping cardiac electrical activity, which is carried out by inserting into a heart a distal portion of a catheter having a plurality of spines mounted at the distal end, each spine having a plurality of electrodes. The method is further carried out by obtaining electrical signal data from the heart via the electrodes, sensing respective intracardiac locations and orientations of the spines, and deriving an electroanatomic map of the heart from the signal data. The electroanatomic map includes a graphic representation of the respective intracardiac locations and orientations of the spines, and also includes distinctive graphical indicia of at least portions of the spines. The method is further carried out by displaying the electroanatomic map, and responsively to the displayed electroanatomic map, adjusting at least one of the locations and orientations of at least one of the spines.

According to an aspect of the method, deriving an electroanatomic map includes assigning respective color codes to the spines, and may include assigning common color codes to respective regions of the spines.

According to another aspect of the method, the graphic representation includes a circle, the center of the circle representing a location of the distal end of the body of the catheter, and radii of the circle representing the locations and orientations of the spines, and bearing the graphical indicia of respective spines.

According to a further aspect of the method, deriving an electroanatomic map also includes calculating electrical or mechanical properties of the heart, and graphically representing locations of the electrical or mechanical properties derived from the spine electrodes and displayed as respective locations within the circle.

According to yet another aspect of the method, calculating electrical or mechanical properties includes determining respective local activation times between at least a portion of the pairs of the spine electrodes.

Other embodiments of the invention provide apparatus for carrying out the above-described method.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily always needed for practicing the present invention. In this instance, well-known circuits, control logic, and the details of computer program instructions for conventional algorithms and processes have not been shown in detail in order not to obscure the general concepts unnecessarily.

Aspects of the present invention may be embodied in software programming code, which is typically maintained in permanent storage, such as a computer readable medium. In a client/server environment, such software programming code may be stored on a client or a server. The software programming code may be embodied on any of a variety of known non-transitory media for use with a data processing system, such as a diskette, hard drive, electronic media or CD-ROM. The code may be distributed on such media, or may be distributed to users from the memory or storage of one computer system over a network of some type to storage devices on other computer systems for use by users of such other systems.

System Description

Figure 1:
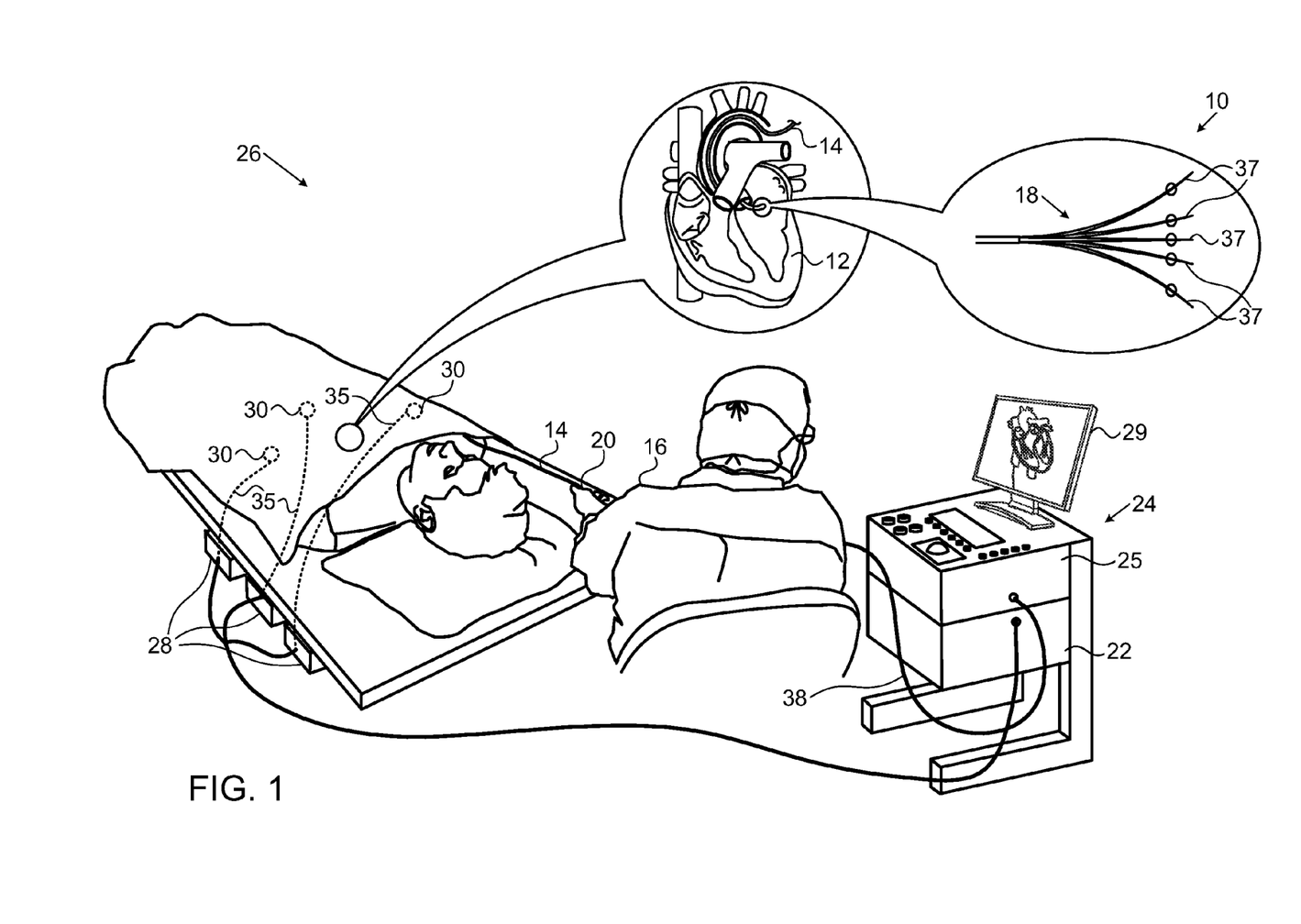
FIG. 1 is a pictorial illustration of a system for performing procedures on a heart of a living subject using a cardiac catheter having multiple spines, which is constructed and operative in accordance with a disclosed embodiment of the invention.

Turning now to the drawings, reference is initially made to FIG. 1, which is a pictorial illustration of a system 10 for performing procedures on a heart 12 of a living subject, which is constructed and operative in accordance with a disclosed embodiment of the invention. The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall at a desired mapping site. Electrical activation maps may then be prepared, according to the methods disclosed in U.S. Pat. Nos. 6,226,542, and 6,301,496, and in commonly assigned U.S. Pat. No. 6,892,091, whose disclosures are herein incorporated by reference. One commercial product embodying elements of the system 10 is available as the CARTO® 3 System, available from Biosense Webster, Inc., 3333 Diamond Canyon Road, Diamond Bar, Calif. 91765.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically about 50° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to treat many different cardiac arrhythmias.

The catheter 14 is a multi-electrode catheter having an elongated body with multiple spines 37, each having mapping and location sensing capabilities as described below. The catheter 14 typically comprises a handle 20, having suitable controls on the handle to enable the operator 16 to steer, position and orient the distal end of the catheter and the location and orientation of the spines as required. To aid the operator 16, the distal portion of the catheter 14 contains position sensors (not shown) that provide signals to a positioning processor 22, located in a console 24. The catheter described in the above-noted U.S. Pat. No. 6,961,602, having five spines, is suitable for use as the catheter 14. This catheter is available as the Pentaray™ catheter or probe from Biosense Webster.

In one embodiment, the catheter 14 comprises an elongated body having a proximal end, a distal end and at least one lumen extending longitudinally therethrough, and a mapping assembly mounted at the distal end of the catheter body and comprising at least two spines. Each spine has a proximal end attached at the distal end of the catheter body and a free distal end. Each spine comprises a support arm having shape memory, a non-conductive covering in surrounding relation to the support arm, at least one location sensor mounted in the distal end of the spine, a plurality of electrodes mounted on the distal end of the spine and electrically isolated from the support arm, and a plurality of electrode lead wires extending within the non-conductive covering, each electrode lead wire being attached to a corresponding one of the electrodes. Optional additional location sensors (not shown) may be disposed on the shaft of the catheter 14 proximal to the spines.

Ablation energy and electrical signals can be conveyed to and from the heart 12 through an optional ablation electrode 32 located at or near the distal tip 18 via cable 34 to the console 24. While a single ablation electrode 32 is shown, more than one can be present. Pacing signals and other control signals may be conveyed from the console 24 through the cable 34 and the ablation electrode 32 to the heart 12. Sensing and ablation electrodes 33 may be disposed generally near at the distal tip 18 have connections to the console 24.

Wire connections 35 link the console 24 with body surface electrodes 30 and other components of a positioning subsystem. A temperature sensor (not shown), typically a thermocouple or thermistor, may be mounted on or near the ablation electrodes at the distal tip 18.

The console 24 may contain one or more ablation power generators 25. The catheter 14 may be adapted to conduct ablative energy to the heart using any known ablation technique, e.g., radiofrequency energy, ultrasound energy, and laser-produced light energy. Such methods are disclosed in commonly assigned U.S. Pat. Nos. 6,814,733, 6,997,924, and 7,156,816, which are herein incorporated by reference.

The positioning processor 22 is an element of a positioning system 26 of the system 10 that measures location and orientation coordinates of the catheter 14.

In one embodiment, the positioning system 26 comprises a magnetic position tracking arrangement that determines the position and orientation of the catheter 14 by generating magnetic fields in a predefined working volume its vicinity and sensing these fields at the catheter using field generating coils 28 and may include impedance measurement, as taught, for example in U.S. Patent Application Publication No. 2007/0060832, which is herein incorporated by reference. The positioning system 26 may be enhanced by position measurements using the impedance measurements described in U.S. Pat. No. 7,536,218, which is herein incorporated by reference.

As noted above, the catheter 14 is coupled to the console 24, which enables the operator 16 to observe and regulate the functions of the catheter 14. Console 24 includes a processor, preferably a computer with appropriate signal processing circuits. The processor is coupled to drive a monitor 29. The signal processing circuits typically receive, amplify, filter and digitize signals from the catheter 14, including signals generated by the above-noted sensors and a plurality of location sensing electrodes (not shown) located distally in the catheter 14. The digitized signals are received and used by the console 24 and the positioning system 26 to compute the position and orientation of the catheter 14 and to analyze the electrical signals from the electrodes.

Typically, the system 10 includes other elements, which are not shown in the figures for the sake of simplicity. For example, the system 10 may include an electrocardiogram (ECG) monitor, coupled to receive signals from one or more body surface electrodes, so as to provide an ECG synchronization signal to the console 24. As mentioned above, the system 10 typically also includes a reference position sensor, either on an externally-applied reference patch attached to the exterior of the subject's body, or on an internally-placed catheter, which is inserted into the heart 12 maintained in a fixed position relative to the heart 12. Conventional pumps and lines for circulating liquids through the catheter 14 for cooling the ablation site are provided.

Figure 2:
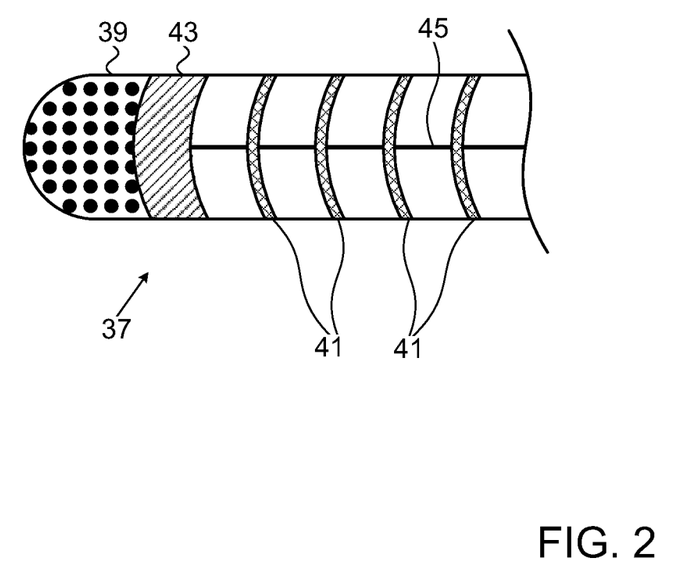
FIG. 2 is a detailed view of one of the spines of the catheter shown in FIG. 1, in accordance with an embodiment of the invention.

Reference is now made to FIG. 2, which is a detailed view of one of the spines 37 (FIG. 1), showing a typical electrode configuration in accordance with an embodiment of the invention. The configuration comprises a tip electrode 39, usable for both sensing and ablation, four ring electrodes 41, used as sensing electrodes to detect electrophysiologic signals in the heart, and a temperature sensor 43, which is used when the catheter 14 is in an ablation mode. However, in different embodiments of the spines 37, the sensing electrodes and ablation electrodes may vary in number, configuration, and distribution in many combinations. A cable 45 communicates signals between the electrodes, sensors and the console 24 (FIG. 1). With the multiple electrodes distributed in several spines 37, it is possible to collect signals from many locations simultaneously.

In other known electrophysiological catheters, the electrodes are located along a straight shaft with known distances separating individual electrodes. However, in the embodiments of FIG. 1 and FIG. 2, multiple electrodes are positioned in different spines. The distribution of spines when in contact with tissue may vary in different sessions, or even in the same session as the catheter is manipulated by the operator. As a result the distances between electrodes on different spines may vary, and generally are not uniform during the signal collection (mapping) process.

In order to facilitate understanding of the significance and the relevant characteristics of a large number of signals, embodiments of the invention present them in a form that color-coordinates with the electrode arrangements of the spines and their respective locations, e.g., by color-coding the spines and tracings derived from the spines, respectively.

The displays described herein can be achieved using the above-noted Carto 3 System, which can be modified by those skilled in the art in order to apply the principles of the invention.

Figure 3:
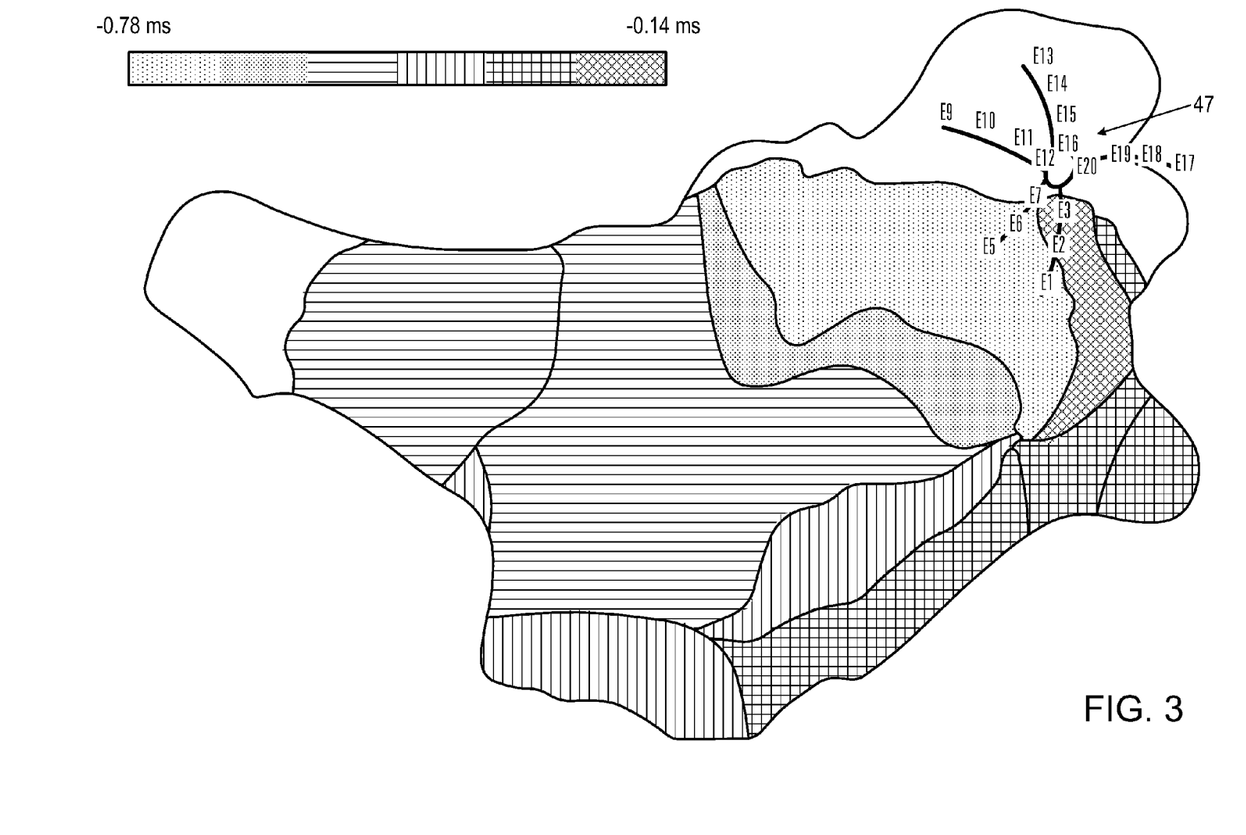
FIG. 3 is a display of a heart showing a multi-spine tip a catheter in accordance with an embodiment of the invention.

Reference is now made to FIG. 3, which is a display of a left atrium of a heart showing the multi-spine tip 47 of a Pentaray catheter in accordance with an embodiment of the invention. Sets of four electrodes on each of the five spines are shown. Each electrode is assigned a designation E1-E20. For example, the four electrodes on spine 51 are numbered E17-E20. This nomenclature is helpful in understanding the recording and display configurations of the electrodes as discussed below. For example, in a bipolar configuration, wherein a signal is measured between electrodes E11, E12, the notation "E11-E12" is used to indicate the pair of electrodes. Electrode pair E10-E11 and electrode pair E11-E12 are adjacent one another. Such configurations may be referred to herein as "adjacent electrode pairs". Electrode pairs E13-E14 and E14-E15 constitute another example of adjacent electrode pairs.

Figure 4:
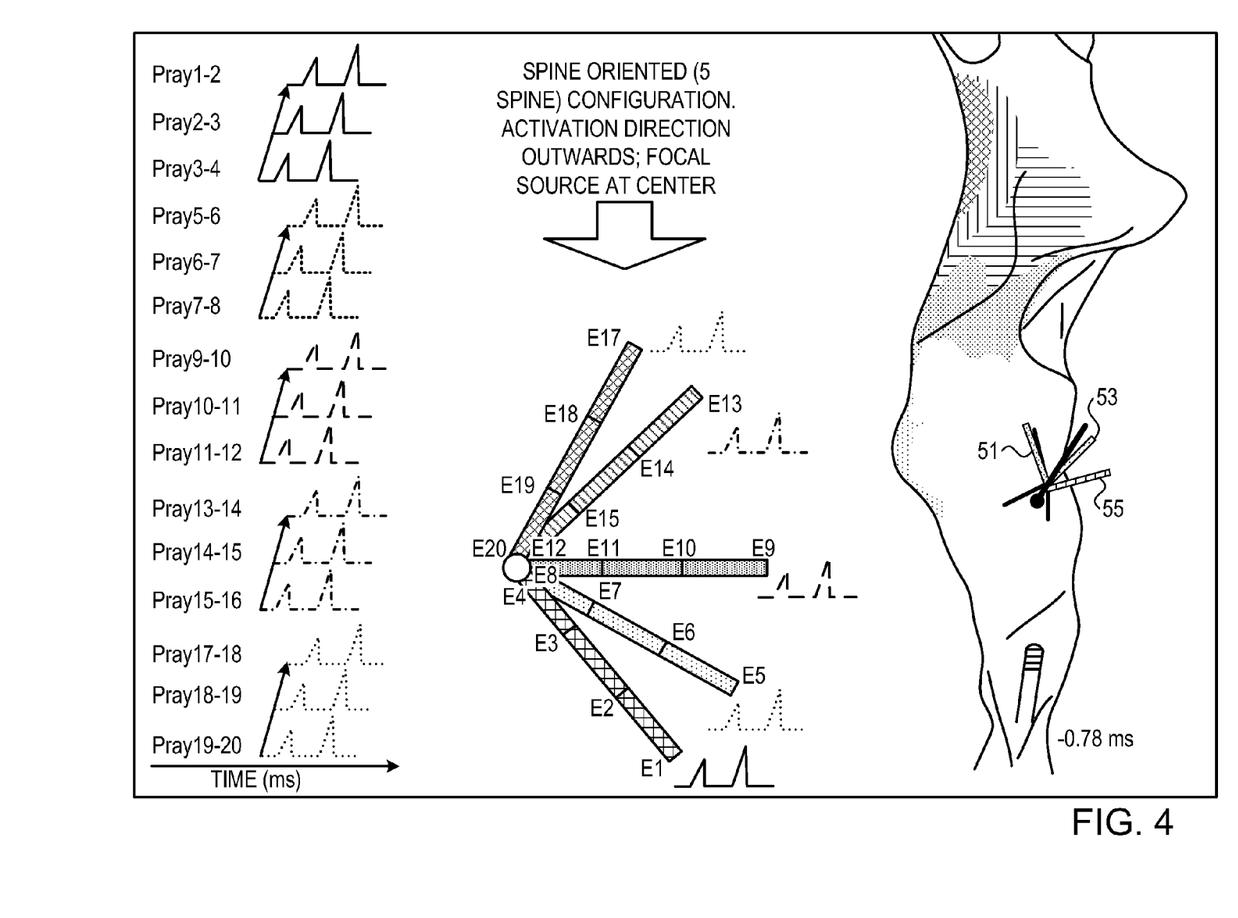
FIG. 4 is a composite diagram, showing electrical signals measured by a multi-spine catheter in accordance with an embodiment of the invention.

Reference is now made to FIG. 4, which is an exemplary composite diagram including a screen display of a right atrium of a heart, showing electrical signals measured by a multi-spine catheter in accordance with an embodiment of the invention. Bipolar signal tracings taken from five spines correspond to five waveform sets, respectively in the left portion of the Figure. The actual screen display may be color-coded for ease of recognition by the operator 16 (FIG. 1) or by an analyst evaluating the display off-line. This is a "spine-oriented" display, in that the waveform groups indicate signals taken from segments of each spine, respectively. Accordingly, on an actual screen display, each spine typically has its own color code.

In FIG. 4, (also in FIG. 5 and FIG. 6, described below), an enlarged view of the spines is at the center. The spines are presented in different hatching patterns to represent different display colors. Waveform groups at the left are presented in different line patterns, again to indicate different colors. To assist the reader, a juxtaposition of a waveform having a particular line pattern and a spine or portion thereof signifies that the two juxtaposed objects would be displayed in the same color on a screen display. A juxtaposition of this sort is shown by waveform 58 adjacent to electrode E17 on spine 51, signifying an association and color coordination between spine 51 and the lowermost group of three waveforms at the upper right of the figure. The lowermost group represents a set of three signals taken from electrodes E17-E18, E18-E19 and E19-E20 of spine 51, all of which are shown in the same line pattern, and would typically be displayed in the same color as the spine 51. The spine 51 appears together with spines 53, 55 at a particular location on a representation of the right atrium in the right portion of the Figure, where it would typically be displayed in the same color as the lowermost group of waveforms. There are, as noted above, 5 spines. Some are intentionally not distinguished by reference numerals for clarity of presentation.

Figure 5:
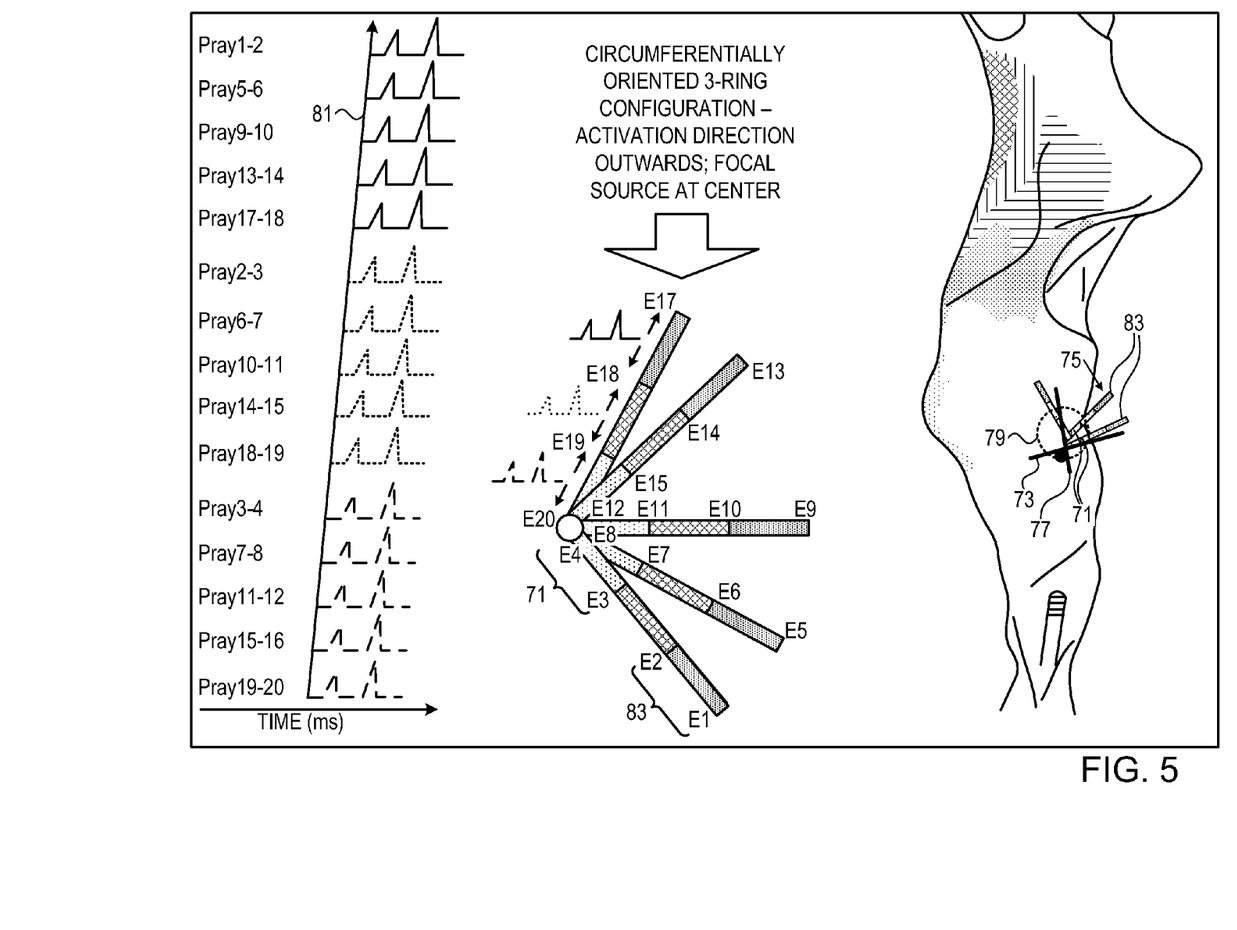
FIG. 5 is another composite diagram, showing electrical signals measured by a multi-spine catheter in accordance with an embodiment of the invention.

Reference is now made to FIG. 5, which is another composite diagram similar to FIG. 4, showing electrical signals measured by a multi-spine catheter in accordance with an embodiment of the invention. This display differs from that shown in FIG. 4, in that waveform sets 65, 67, 69 are "circumferentially oriented", in that the bipolar signals in each waveform set are taken from corresponding intervals along a plurality of the spines, i.e., inner, outer and intermediate regions on the spines. For example the waveform set 69 maps to inner regions 71 of spines 73, 75, 77. The regions 71 define an arc of a ring 79 that is generally centered on the shaft of the catheter 14 (FIG. 1). Arrow 81 indicates a propagation vector from a focal source near the center of the ring toward electrodes located on outer regions 83 of the spines.

Figure 6:
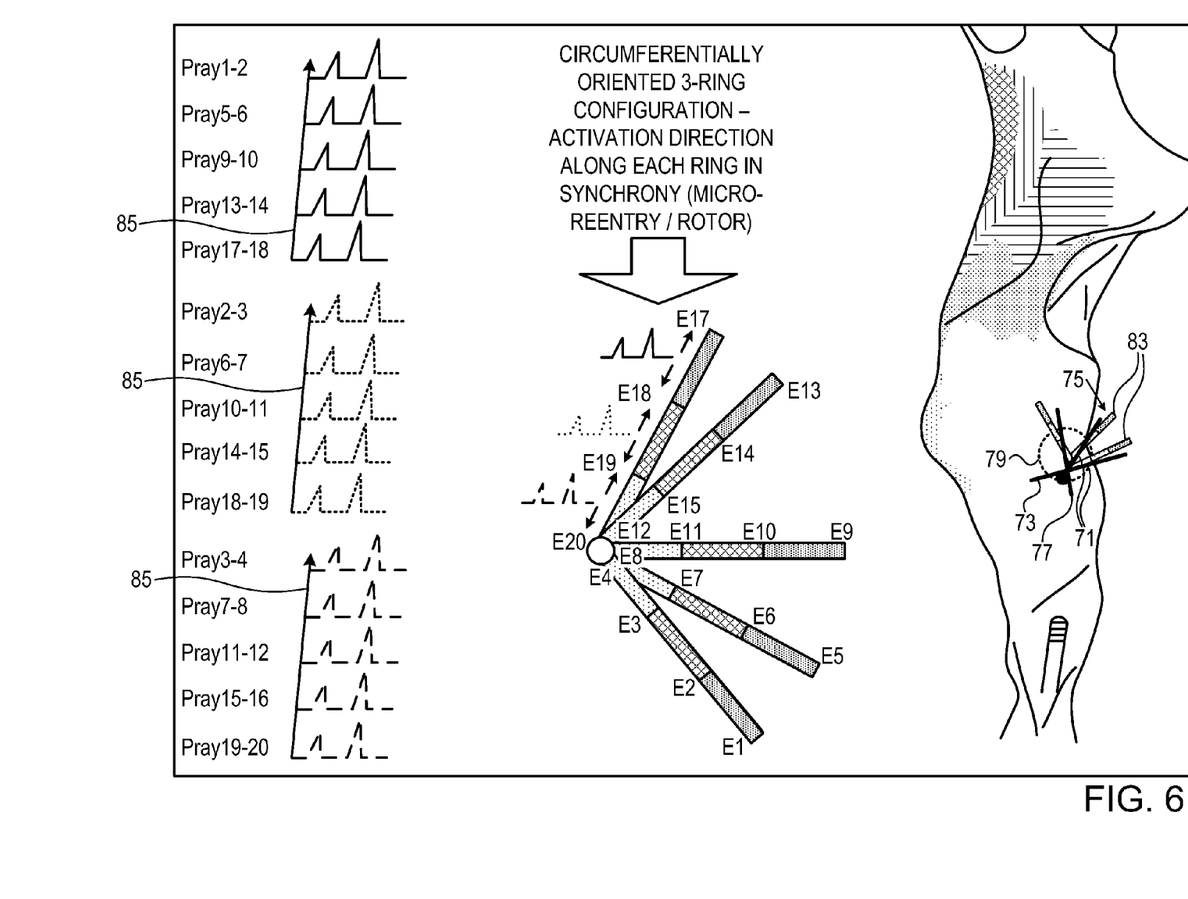
FIG. 6 is another composite diagram, showing electrical signals measured by a multi-spine catheter in accordance with an embodiment of the invention.

Reference is now made to FIG. 6, which is another composite diagram similar to FIG. 4, showing electrical signals measured by a multi-spine catheter in accordance with an embodiment of the invention. The orientation of the waveform sets is the same as that of FIG. 5. However, in this display, a micro-reentry pattern of propagation is seen, emphasized by the phase variations within each waveform set and the timing template similarity of the three waveform sets in the upper left portion of the pane. This is emphasized by arrows 85, which can be understood as vectors with reference to the nomenclature shown in FIG. 3.

Figure 7:
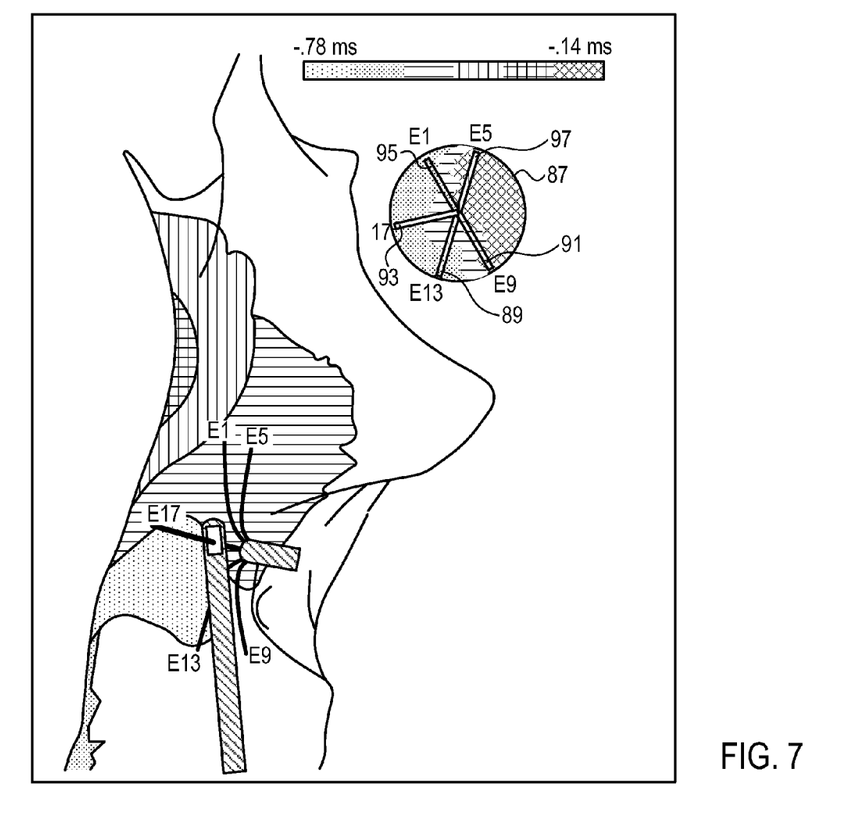
FIG. 7 is a screen display of a heart, showing electrical signals measured by a multi-spine catheter in accordance with an embodiment of the invention.

Reference is now made to FIG. 7, which is a display of a heart, showing electrical signals measured by a multi-spine catheter in accordance with an embodiment of the invention. In this example, there is a circle 87 having five colored radii 89, 91, 93, 95, 97, representing respective spines as they would appear from a perspective along the axis of the shaft of the catheter 14 (FIG. 1). The orientation of the spines is determinable from the orientation of the corresponding radii 89, 91, 93, 95, 97. Typically, the operator wants the spines to be arranged approximately symmetrically, and the operator may manually rotate or translate the catheter 14 until, from the displayed diagram, this is the case. Alternative arrangements can be achieved by the operator by appropriate manipulations of the catheter 14. Availability of a diagram such as shown in FIG. 7 enables the operator to quickly understand the orientation and inter-positional relation between the spines and if needed to adjust the orientation of the spines without having to manipulate or rotate a 3-D map in which the probe is indicated.

The interior of the circle 87 contains a regional local activation time (LAT) map of the area covered by the Pentaray electrodes. The LAT value is calculated per each Pentaray signal pair and the relative activation pattern is color-coded within the Pentaray area per each catheter location. The display of FIG. 7 integrates the Pentaray spines' physical arrangement and the activation pattern of the signals within one icon, enabling the operator to easily and continually evaluate the regional LAT during the procedure. This type of display is adaptable to other electroanatomic maps, in which different parameters relating to cardiac function or pathology are measured locally or regionally and displayed graphically.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method of mapping cardiac electrical activity comprising the steps of:
    inserting into a heart a distal portion of a catheter comprising an elongated body having a distal end, and a plurality of spines mounted at the distal end, each of the spines having a proximal end attached at the distal end of the body, a free end, and a plurality of electrodes;
    obtaining electrical signal data from the heart via the electrodes;
    sensing respective intracardiac locations and orientations of the spines;
    deriving an electroanatomic map of the heart from the signal data, wherein the electroanatomic map comprises a graphic representation comprising a circle having a center representing a location of a distal end of the body of the catheter and a plurality of radii representing intracardiac locations and orientations of the spines, and further comprises distinctive graphical indicia of the spines, wherein the graphic representation shows a non-equiangular distribution of the radii about the center corresponding to a non-symmetrical arrangement of the spines within the heart;
    displaying the electroanatomic map; and
    responsively to the displayed electroanatomic map, adjusting at least one of the locations and orientations of at least one of the spines so as to bring the arrangement of the spines more nearly into symmetry.

2. The method according to claim 1, wherein deriving an electroanatomic map comprises assigning respective color codes to the spines.

3. The method according to claim 1, wherein deriving an electroanatomic map comprises assigning common color codes to respective regions of the spines.

4. The method according to claim 1, wherein deriving an electroanatomic map further comprises calculating electrical or mechanical properties of the heart, and graphically representing locations of the electrical or mechanical properties relative to the distal end of the body of the catheter as respective locations within the circle.

5. The method according to claim 4, wherein calculating electrical or mechanical properties comprises determining respective local activation times of all pairs of the electrodes.

* * * * *